United States Patent
Taylor (10) Patent No.: US 8,486,935 B2
(45) Date of Patent: Jul. 16, 2013

(54) XINAFOATE SALT OF N4-(2,2-DIFLUORO-4H-BENZO[1,4]OXAZIN-3-ONE)-6-YL]-5-FLUORO-N2-[3-(METHYLAMINOCARBO-NYLMETHYLENEOXY)PHENYL]2,4-PYRIMIDINEDIAMINE

(75) Inventor: Stefan Colin John Taylor, Sandwich (GB)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/467,850

(22) Filed: May 9, 2012

(65) Prior Publication Data

US 2012/0316160 A1   Dec. 13, 2012

Related U.S. Application Data

(63) Continuation of application No. 12/676,075, filed as application No. PCT/IB2008/002288 on Aug. 27, 2008, now Pat. No. 8,193,181.

(60) Provisional application No. 60/970,030, filed on Sep. 5, 2007.

(51) Int. Cl.
 *A61K 31/538* (2006.01)
(52) U.S. Cl.
 USPC ........................................ 514/230.5; 544/105

(58) Field of Classification Search
 USPC ....................................................... 514/230.5
 See application file for complete search history.

(56) References Cited

FOREIGN PATENT DOCUMENTS

| WO | WO 91/11172 | 8/1991 |
|---|---|---|
| WO | WO 94/02518 | 2/1994 |
| WO | WO 98/55148 | 12/1998 |
| WO | WO 99/55319 | 11/1999 |
| WO | WO 03/063794 | 8/2003 |
| WO | WO 2005/012294 | 2/2005 |
| WO | WO 2008/000839 | 1/2008 |

OTHER PUBLICATIONS

International Search Report dated Mar. 3, 2009, from International Application No. PCT/IB2008/002288.

*Primary Examiner* — Kahsay T Habte
(74) *Attorney, Agent, or Firm* — Travis Young; Klarquist Sparkman, LLP (57) ABSTRACT

The present invention relates to the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine. This compound is a suitable drug substance and is useful in the treatment of conditions including asthma.

2 Claims, 6 Drawing Sheets

Reflectance/Wavenumber (cm-1)

XINAFOATE SALT OF N4-(2,2-DIFLUORO-4H-BENZO[1,4]OXAZIN-3-ONE)-6-YL]-5-FLUORO-N2-[3-(METHYLAMINOCARBO-NYLMETHYLENEOXY)PHENYL]2,4-PYRIMIDINEDIAMINE

CROSS REFERENCE TO RELATED APPLICATIONS

This application is a continuation of U.S. patent application Ser. No. 12/676,075, filed Mar. 2, 2010, which is the U.S. National Stage of International Application No. PCT/IB08/002,288, filed Aug. 27, 2008, which claims the benefit of the earlier filing date of U.S. Provisional Application No. 60/970,030, filed on Sep. 5, 2007. The entire disclosures of these prior applications are incorporated herein by reference.

The present invention relates to the xinafoate salt of N4-[(2,2-difluoro-4Hbenzo[1,4]oxazin-3-one)-6-yl]-5-fluoro-N2-[3-(methylaminocarbonylmethylene oxy)phenyl]-2,4-pyrimidinediamine and to pharmaceutical compositions comprising and to processes for making such a compound. The invention further relates to the use of the salt and its compositions in the treatment of various conditions, particularly in the treatment of inflammatory conditions such as asthma.

The compound N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine, having the structural formula (I):

(I)

is disclosed in WO-A-03/063794 as Example 7.3.907 on page 440. The compound, which is also known as 2-{3-[4-(2,2-Difluoro-3-oxo-3,4-dihydro-2H-benzo[1,4]oxazin-6-ylamino)-5-fluoro-pyrimidin-2-ylamino]phenoxy}N-methyl-acetamide, is one of a genus of compounds which are disclosed to be inhibitors of Syk kinase and therefore useful in the treatment of inflammatory conditions such as chronic obstructive pulmonary disease (COPD). It is noted that the compounds can be formulated in a pharmaceutical composition in their free form or in the form of a hydrate, solvate, N-oxide or pharmaceutically acceptable salt (pages 70-71). A pharmaceutical composition suitable for inhalation comprising one of the compounds and a suitable powder base, such as lactose or starch, is specifically mentioned (page 72).

If a compound is to be developed as a drug, it is important to provide a form of that compound (commonly known as a drug substance) which can be reliably prepared and purified on a large scale, which is stable and which does not degrade on storage. Such characteristics are normally found in a drug substance which is crystalline and of high melting point; a high-melting point crystalline solid tends to be easy to purify by recrystallization and stable on storage. Furthermore, the drug substance must be suitable for formulation in a dosage form chosen according to the intended route of administration. For formulation as a dry powder suitable for inhalation, nonhygroscopicity is particularly important in order to obtain good flow characteristics. Compatibility with conventional excipients such as lactose and starch is a further mandatory requirement. Further, the drug substance will usually require processing in order to achieve a particle size suitable for inhalation and any crystalline form must be stable during such processing so that the properties of the final product are predictable and reliable. In short, whether or not a compound is suitable for commercialisation as a drug is dependent on finding a form of the compound with a unique combination of properties determined according to the intended route of administration.

The free form of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine disclosed in WO-A-03/063794 is not suitable for commercialisation as a drug since it is predominantly amorphous, or exists in a disordered crystalline form and is prone to hydration and solvation. There is therefore a need to provide a new form of N4-[(2,2-difluoro-4Hbenzo[1,4]oxazin-3-one)-6-yl]-5-fluoro-N2-[3-(methylaminocarbonylmethyleneoxy)phenyl]-2,4-pyrimidinediamine which has the required characteristics. Salt formation is one possible avenue of enquiry, but the properties of salts are hard to predict and, worse still, the compound will not form salts with many common pharmaceutically acceptable acids. Many salt forms that do form, such as the mesylate, fumarate, hemifumarate, hydrobromide, hydrochloride, D-tartrate, hemisulphate and isethionate salts, have one or more unsatisfactory properties such as poor crystallinity and the propensity to form hydrates and/or solvates.

As a result of extensive research, however, it has now been possible to design a form of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine which has a unique set of characteristics making it ideal for administration in a dry powder formulation. The xinafoate salt is highly crystalline, has a melting point of about 233° C., is essentially non-hygroscopic and can be micronised by jet milling without inducing any change in crystalline form. Furthermore, it shows good stability when blended with lactose monohydrate and stored under aggressive conditions of heat and humidity and the lactose blend aerosolises well when used in conjunction with standard dry powder inhalers.

The present invention therefore provides, in a first aspect, the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine, having the structure shown in Formula (II) below. Xinafoate is the common name for 1-hydroxy-2-naphthoate. It should be noted that this molecule can be depicted in several different tautomeric forms depending on the location of the proton, all of which are equivalent.

(II)

The invention further provides: the xinafoate salt of N4-[(2,2-difluoro-4Hbenzo[1,4]oxazin-3-one)-6-yl]-5-fluoro-N2-[3-(methylaminocarbonylmethyleneoxy)phenyl]-2,4-pyrimidinediamine for use as a medicament; the xinafoate salt of N4-[(2,2-difluoro-4H-benzo[1,4]oxazin-3-one)-6-yl]-5-fluoro-N2-[3-(methylaminocarbonyl methyleneoxy)phenyl]-2,4-pyrimidinediamine for use in treating a condition for which a Syk kinase inhibitor is indicated; the use of the xinafoate salt of N4-[(2,2-difluoro-4Hbenzo[1,4]oxazin-3-one)-6-yl]-5-fluoro-N2-[3-(methylaminocarbonylmethyleneoxy)phenyl]-2,4-pyrimidinediamine for the manufacture of a medicament to treat a disease for which a Syk kinase inhibitor is indicated; a pharmaceutical composition comprising the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine and a pharmaceutically acceptable excipient; a pharmaceutical composition for the treatment of a disease for which a Syk kinase inhibitor is indicated comprising the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine; and a method of treating a disease for which a Syk kinase inhibitor is indicated in a mammal comprising administering to the mammal in need thereof a therapeutically effective amount of the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine. Preferred diseases for which a Syk inhibitor is indicated are inflammatory respiratory diseases such as asthma, rhinitis and COPD, particularly asthma.

The xinafoate salt can be prepared by dissolving N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine and between 1 and 1.1 molar equivalents 1-hydroxy-2-naphthoic acid in the minimum amount of a suitable organic solvent and cooling the solution slowly, optionally with stirring, until the salt precipitates from the solution. Suitable solvents are acetone, acetonitrile and methyl ethyl ketone (MEK), each optionally containing a small amount of water (e.g. less than 10%). Methyl ethyl ketone is particularly suitable and is preferably used with about 5% by volume of water. The reactants are typically dissolved in the solvent at a temperature higher than room temperature but below the boiling point of the solvent.

N4-[(2,2-Difluoro-4H-benzo[1,4]oxazin-3-one)-6-yl]-5-fluoro-N2-[3-(methylaminocarbonylmethyleneoxy)phenyl]-2,4-pyrimidinediamine may be prepared by the general and specific methods disclosed in WO-A-03/063794. It may, for example, be prepared by reacting a compound of formula (III)

with a compound of formula

(IV)

The reaction is typically carried out in a suitable solvent, preferably an alcohol such as isoamyl alcohol or isopropyl alcohol, and in the presence of an acid catalyst such as trifluoroacetic acid. The reaction is best carried out at an elevated temperature. If amyl alcohol is selected as the solvent, for example, a temperature of about 100° C. is preferred.

A compound of formula (III) may be prepared by the route set out in Scheme 1 below.

Scheme 1

A compound of formula (III) may be prepared by reducing the nitro group in a compound of formula (V). In a preferred procedure, hydrogenation is used. Typically, a solution of the compound of formula (V) in a suitable organic solvent, such as a mixture of ethanol (EtOH) and ethyl acetate (EtOAc), is treated with a hydrogenation catalyst, such as palladium on carbon, and exposed to hydrogen gas. The hydrogen is usually applied at a pressure above atmospheric, preferably at 30 pounds per square inch (psi).

A compound of formula (V) may be prepared by condensing the acid of formula (VI) with methylamine, or a salt thereof (such as the hydrochloride salt). Any condensing agent suitable for the formation of amide bonds may be used in principle, but the use of 2-(1H-benzatriazole-1-yl)-1,1,3,3-tetramethyluronium tetrafluoroborate (TBTU) is preferred. The condensation catalysed by TBTU is carried out in a suitable organic solvent, such as N,N-dimethylformamide (DMF), and in the presence of a base such as N,N diisopropylethylamine (DIPEA).

A compound of formula (VI) may be prepared by alkylating 3-nitrophenol (VII) with bromoacetic acid. The reaction is typically carried out in a suitable solvent, such as water or aqueous ethanol (EtOH), in the presence of a base, such as sodium hydroxide (NaOH), and at elevated temperature, e.g. at the reflux temperature of the chosen solvent.

A compound of formula (IV) can be prepared by the route set out in Scheme 2 below.

a suitable organic solvent, such as ethanol (EtOH) or a mixture of ethanol and tetrahydrofuran (THF), is treated with a base such as sodium hydrogencarbonate.

A compound of formula (VIII) may be prepared by the reducing the nitro group in a compound of formula (IX). In a preferred procedure, hydrogenation is used. Typically, a solution of the compound of formula (IX) in a suitable organic solvent, such as ethanol (EtOH), is treated with a hydrogenation catalyst, such as palladium on carbon, and exposed to hydrogen gas. The hydrogen is usually applied at a pressure above atmospheric, preferably at 30 pounds per square inch (psi).

A compound of formula (IX) may be prepared by the cyclisation of a compound of formula (X). In a typical procedure, a solution of a compound of formula (X) in a suitable organic solvent, such as N,N-dimethylformamide (DMF) or isopropyl acetate, is treated with a base, such as potassium carbonate, and heated, for example at the reflux temperature of the solvent. When DMF is chosen as solvent, a temperature of about 120° C. is preferred. When isopropyl acetate is chosen as solvent, a temperature of about 85° C. is preferred.

A compound of formula (X) may be prepared by acylation of the aniline of formula (XI) with 2-bromo-2,2-difluoroacetyl chloride. The reaction is preferably carried out in a suitable organic solvent, such as dichloromethane (DCM) or acetonitrile, in the presence of a base, such as triethylamine. The reaction is exothermic and cooling, for example to 0° C., may therefore be required.

Scheme 2

A compound of formula (IV) may be prepared by reacting a compound of formula (VIII) with 5-fluoro-2,4-dichloropyrimidine. In a typical procedure, a solution of the reactants in The present invention includes all crystalline and pharmaceutically acceptable isotopically-labeled forms of the xinafoate salt of N4-[(2,2-difluoro-4H-benzo[1,4]oxazin-3- one)-6-yl]-5-fluoro-N2-[3-(methylaminocarbonylmethyleneoxy)phenyl]-2,4-pyrimidinediamine. In an isotopically-labeled form, one or more atoms are replaced by an atom or atoms having the same atomic number, but an atomic mass or mass number different from the atomic mass or mass number which predominates in nature.

Suitable isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O; and sulphur, such as $^{35}$S. Certain isotopically-labeled compounds, such as those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O, and $^{13}$N, can be useful in Positron Emission Topography (PET) studies for examining substrate receptor occupancy. Isotopically-labeled compounds can generally be prepared by conventional techniques known to those skilled in the art or by processes analogous to those described in the accompanying Examples and Preparations using an appropriate isotopically-labeled reagent in place of the non-labeled reagent previously employed.

N4-[(2,2-Difluoro-4H-benzo[1,4]oxazin-3-one)-6-yl]-5-fluoro-N2-[3-(methylaminocarbonylmethyleneoxy)phenyl]-2,4-pyrimidinediamine is a Syk kinase inhibitor and is able to inhibit the degranulation of immune cells, such as mast, basophile, neutrophil and/or eosinophil cells. It may be useful, in the form of the xinafoate salt disclosed by the present invention and otherwise, in the treatment of the following conditions:

Treatable obstructive, restrictive or inflammatory airways diseases of whatever type, etiology, or pathogenesis, in particular an obstructive, restrictive or inflammatory airways disease such as:

asthma, in particular atopic asthma, allergic asthma, atopic bronchial lgE-mediated asthma, non-atopic asthma, bronchial asthma, non-allergic asthma, essential asthma, true asthma, intrinsic asthma caused by pathophysiologic disturbances, essential asthma of unknown or inapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma;

bronchial hyper-responsivity to environmental agents;

rhinitis or sinusitis of whatever type, etiology, or pathogenesis, in particular seasonal allergic rhinitis, perennial allergic rhinitis, perennial rhinitis, vasomotor rhinitis, post-nasal drip, purulent or nonpurulent sinusitis, acute or chronic sinusitis and ethmoid, frontal, maxillary, or sphenoid sinusitis;

chronic obstructive pulmonary disease (COPD), chronic obstructive lung disease (COLD), chronic obstructive airways disease (COAD) or small airways obstruction of whatever type, etiology, or pathogenesis, in particular chronic bronchitis, pulmonary emphysema, bronchiectasis, cystic fibrosis, bronchiolitis obliterans, bronchiolitis obliterans organizing pneumonia (BOOP), chronic organizing pneumonia (COP), bronchiolitis fibrosa obliterans, follicular bronchiolitis or dyspnea associated therewith;

bronchitis of whatever type, etiology, or pathogenesis, in particular acute bronchitis, acute laryngotracheal bronchitis, arachidic bronchitis, catarrhal bronchitis, croupus bronchitis, chronic bronchitis, dry bronchitis, infectious asthmatic bronchitis, productive bronchitis, *staphylococcus* or streptococcal bronchitis and vesicular bronchitis;

bronchiectasis of whatever type, etiology, or pathogenesis, in particular cylindric bronchiectasis, sacculated bronchiectasis, fusiform bronchiectasis, capillary bronchiectasis, cystic bronchiectasis, cystic fibrosis, Kartageners's syndrome, dry bronchiectasis or follicular bronchiectasis;

pulmonary eosinophilic syndromes of whatever type, etiology, or pathogenesis, in particular acute eosinophilic pneumonia (idiopathic or due to drugs or parasites), simple pulmonary eosinophilia, Loeffler's syndrome, tropical pulmonary eosinophilia, chronic eosinophilic pneumonia, allergic bronchopulmonary mycosis, allergic bronchopulmonary aspergillosis (ABPA), Churg-Strauss syndrome or idiopathic hypereosinophilic syndrome;

interstitial lung diseases (ILD) or pulmonary fibrosis of whatever type, etiology, or pathogenesis, in particular idiopathic pulmonary fibrosis, crytogenic fibrosing alveolitis, fibrosing alveolitis, ILD or pulmonary fibrosis associated with connective tissue disease (systemic lupus erythematosis, mixed connective tissue disease, polymyositis, dermatomyositis, Sjörgen's syndrome, systemic sclerosis, scleroderma, rheumatoid arthritis), usual interstitial pneumonia (UIP), desquamative interstitial pneumonia (DIP), granulomatous lung disease, sarcoidosis, Wegener's granulomatosis, histiocytosis X, Langerhan's cell granulomatosis, hypersensitivity pneumonitis, extrinsic allergic alveolitis, silicosis, chronic eosinophilic pneumonia, lymphangiolyomatosis, drug-induced ILD or pulmonary fibrosis, radiation-induced ILD or pulmonary fibrosis, alveolar proteinosis, graft-versus-host-disease (GVHD), lung transplant rejection, ILD or pulmonary fibrosis due to environmental/occupational exposure, BOOP, COP, bronchiolitis fibrosa obliterans, follicular bronchiolitis, idiopathic acute interstitial pneumonitis (Hamman Rich syndrome) or alveolar hemorrhage syndromes;

pneumoconiosis of whatever type, etiology, or pathogenesis, in particular aluminosis or bauxite workers' disease, anthracosis or miners' asthma, progressive massive fibrosis (PMF), asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma or talc pneumoconiosis;

Acute Respiratory Distress Syndrome (ARDS), adult respiratory distress syndrome or acute lung injury of whatever type, etiology, or pathogenesis;

aspiration disorders of whatever type, etiology, or pathogenesis leading to aspiration pneumonitis or aspiration pneumonia;

alveolar hemorrhage of whatever type, etiology, or pathogenesis, in particular a member of the group consisting of idiopathic pulmonary hemosiderosis, alveolar hemorrhage due to drugs or other exogenous agents, alveolar hemorrhage associated with HIV or bone marrow transplant or autoimmune alveolar hemorrhage (e.g. associated with systemic lupus erythematosis, Goodpasture's syndrome, Wegener's granulomatosis, microscopic polyangiitis, Churg-Strauss syndrome, pauci-immune glomerulonephritis);

acute or chronic laryngitis or pharyngitis;

cough of whatever type, etiology, or pathogenesis in particular idiopathic cough or cough associated with gastro-esophageal reflux disease (GERD), drugs, bronchial hyper-responsivity, asthma, COPD, COLD, COAD, bronchitis, bronchiectasis, pulmonary eosinophilic syndromes, pneumoconiosis, interstitial lung disease, pulmonary fibrosis, aspiration disorders, rhinitis, laryngitis or pharyngitis;

anaphylaxis and type 1 hypersensitivity reactions of whatever aetiology;

atopic, allergic, autoimmune or inflammatory skin disorders of whatever type, etiology, or pathogenesis, in particular atopic dermatitis, allergic dermatitis, contact dermatitis, allergic or atopic eczema, lichen planus, mastocytosis, erythema nodosum, erythema multiforme, benign familial pemphigus, pemphigus erythematosus, pemphigus foliaceus, and pemphigus vulgaris, bullous pemphigoid, epidermolysis bullosa, dermatitis hepetiformis, psoriasis, immune-mediated urticaria, complement-mediated urticaria, urticariogenic material-induced urticaria, physical agent-induced urticaria, stress-induced urticaria, idiopathic urticaria, acute urticaria, chronic urticaria, angioedema, cholinergic urticaria, cold urticaria in the autosomal dominant form or in the acquired form, contact urticaria, giant urticaria or papular urticaria;

conjunctivitis of whatever type, etiology, or pathogenesis, in particular actinic conjunctivitis, acute catarrhal conjunctivitis, acute contagious conjunctivitis, allergic conjunctivitis, atopic conjunctivitis, chronic catarrhal conjunctivitis, purulent conjunctivitis or vernal conjunctivitis;

multiple sclerosis of whatever type, etiology, or pathogenesis, in particular primary progressive multiple sclerosis or relapsing remitting multiple sclerosis;

autoimmune/inflammatory diseases of whatever type, etiology, or pathogenesis, in particular autoimmune hematological disorders, hemolytic anemia, aplastic anemia, pure red cell anemia, idiopathic thrombocytopenic purpura, rheumatoid arthritis, systemic lupus erythematosus, scleroderma, systemic sclerosis, oolymyalgia rheumatica, dermatomyositis, polymyositis, polychondritis, Wegner's granulomatosis, chronic active hepatitis, myasthenia gravis, Stevens-Johnson syndrome, idiopathic sprue, autoimmune inflammatory bowel diseases, Crohn's disease, ulcerative colitis, endocrine opthalmopathy, Grave's disease, sarcoidosis, alveolitis, chronic hypersensitivity pneumonitis, primary biliary cirrhosis, juvenile diabetes or diabetes mellitus type I, keratoconjunctivitis sicca, epidemic keratoconjunctivitis, glomerulonephritis with or without nephrotic syndrome, acute glomerulonephritis, idiopathic nephrotic syndrome, minimal change nephropathy, autoimmune disorders associated with interstitial lung disease and/or pulmonary fibrosis or autoimmune or inflammatory skin disorders;

inflammatory bowel disease (IBD) of whatever type, etiology, or pathogenesis, in particular collagenous colitis, colitis polyposa, transmural colitis, ulcerative colitis or Crohn's disease (CD);

pulmonary hypertension of whatever type, etiology or pathogenesis including pulmonary arterial hypertension, pulmonary venous hypertension, pulmonary hypertension associated with disorders of the respiratory system and/or hypoxemia, pulmonary hypertension due to chronic thrombotic and/or embolic disease and pulmonary hypertension due to disorders directly affecting the pulmonary vasculature;

arthritis of whatever type, etiology, or pathogenesis, in particular rheumatoid arthritis, osteorthritis, gouty arthritis, pyrophosphate arthropathy, acute calcific periarthritis, chronic inflammatory arthritis, arthritis associated with a connective tissue disorder (e.g. systemic lupus erythematosis, polymyositis, dermatomyositis, systemic sclerosis, scleroderma), sarcoidosis, polymyalgia rheumatica, degenerative arthritis, infectious arthritis, Lyme arthritis, proliferative arthritis, psoriatic arthritis, ankylosing spondylitis, cervical spondylosis, vertebral arthritis, juvenile arthritis (Still's disease), amyloidosis, ankylosing vertebral hyperostosis (Forrestier's disease), Behçet's syndrome, drug-induced arthritis, familial Mediterranean fever, hypermobility syndrome, osteochondritis dessicans, osteochondromatosis, palindromic rheumatism, pigmented villonodular synovitis, relapsing polychondritis, temporomandibular pain dysfunction syndrome or arthritis associated with hyperlipidemia;

an eosinophil-related disorder of whatever type, etiology, or pathogenesis, in particular pulmonary eosinophilic syndromes, aspergilloma, granulomas containing eosinophils, allergic granulomatous angiitis or Churg-Strauss syndrome, polyarteritis nodosa (PAN) or systemic necrotizing vasculitis;

uveitis of whatever type, etiology, or pathogenesis, in particular inflammation of all or part of the uvea, anterior uveitis, iritis, cyclitis, iridocyclitis, granulomatous uveitis, nongranulomatous uveitis, phacoantigenic uveitis, posterior uveitis, choroiditis or chorioretinitis;

septic shock of whatever type, etiology, or pathogenesis;

disorders of bone deposition/resorption, including osteoporosis and osteopenia;

lymphoproliferative disorders (e.g. lymphoma, myeloma);

HIV or AIDs related disorders;

infection, especially infection due to viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3, cytomegalovirus (CMV), influenza, adenoviruses and Herpes viruses including Herpes zoster and Herpes simplex;

yeast and fungal infections wherein the yeast or fungus is sensitive to upregulation by TNF-α or elicits TNF-α production in the host, e.g., fungal meningitis, particularly when administered in conjunction with other drugs of choice for the treatment of systemic yeast and fungus infections, including but are not limited to, polymixins (e.g. Polymycin B), imidazoles (e.g. clotrimazole, econazole, miconazole, and ketoconazole), triazoles (e.g. fluconazole and itranazole) and amphotericins (e.g. Amphotericin B and liposomal Amphotericin B); and Mycobacterial infections e.g. due to *mycobacterium tuberculosis*.

The xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine (henceforth referred to as the compound of the invention) may be administered alone but will generally be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Pharmaceutical compositions suitable for the delivery of the compound of the invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compound of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compound of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the compound of the invention may make up from 1 weight % to 80 weight % of the dosage form, more typically from 5 weight % to 60 weight % of the dosage form.

In addition, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are also generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible tablet ingredients include anti-oxidants, colouring agents, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller compaction to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

The compound of the invention may also be orally administered in the form of a consumable oral film for human or veterinary use. Such a film is typically a pliable water-soluble or water-swellable thin film dosage form which may be rapidly dissolving or mucoadhesive and typically comprises the compound of the invention, a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible film ingredients include anti-oxidants, colouring agents, flavourings and flavour enhancers, preservatives, salivary stimulating agents, cooling agents, cosolvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuum drying.

Solid formulations for oral administration may be formulated to be immediate and/or modified release. Modified release includes delayed, sustained, pulsed, controlled, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line,* 25(2), 1-14, by Verma et al (2001). The use of chewing gum to achieve controlled release is described in WO-A-00/35298.

The compound of the invention may also be administered directly into the blood stream, into muscle, or into an internal organ. Such parenteral administration may be via the intravenous, intraarterial, intraperitoneal, intrathecal, intraventricular, intraurethral, intrasternal, intracranial, intramuscular or subcutaneous route. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Formulations for parenteral administration may be formulated to be immediate and/or modified release. Modified release includes delayed, sustained, pulsed, controlled, targeted and programmed release. Thus compound of the invention may be formulated as a solid, semi-solid or thixotropic liquid for administration as an implanted depot providing modified release of the compound of the invention. Examples of such formulations include drug-coated stents and poly(dl-lactic-coglycolic)acid (PGLA) microspheres.

The compound of the invention may also be administered topically to the skin or mucosa, i.e. dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm. Sci., 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™) injection.

Formulations for topical administration may be formulated to be immediate and/or modified release. Modified release includes delayed, sustained, pulsed, controlled, targeted and programmed release.

The compound of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. Administration in the form of a dry powder from a dry powder inhaler is a particularly preferred form of delivery.

The pressurised container, pump, spray, atomizer or nebuliser contains a solution or suspension of the compound of the invention comprising, for example, ethanol, aqueous ethanol or a suitable alternative agent for dispersing, solubilising or extending release of the active, a propellant(s) as solvent and an optional surfactant, such as sorbitan trioleate, oleic acid or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1-leucine, mannitol or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula I, propylene glycol, sterile water, ethanol and sodium chloride. Alternative solvents which may be used instead of propylene glycol include glycerol and polyethylene glycol.

Suitable flavouring agents, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release includes delayed, sustained, pulsed, controlled, targeted and programmed release.

In the case of dry powder inhalers and aerosols, the dosage unit may be determined by means of a valve which delivers a metered amount. The overall daily dose may be administered in a single dose or, more usually, as divided doses throughout the day.

The compound of the invention may be administered rectally or vaginally, in the form, for example, of a suppository, pessary or enema. Cocoa butter is a traditional suppository base, but various alternatives may be used as appropriate. The compound of the invention may also be administered by the ocular or aural route.

The compound of the invention may be combined with a soluble macromolecular entity, such as a cyclodextrin or a suitable derivative thereof or a polyethylene glycol-containing polymer, in order to improve its solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in WO-A-91/11172, WO-A-94/02518 and WO-A-98/55148.

For administration to human patients, the total daily dose of the compound of the invention will typically be in the range 0.002 mg/kg to 100 mg/kg depending, of course, on the mode of administration. The total daily dose may be administered in single or divided doses and may, at the physician's discretion, fall outside of the typical range given herein.

For the avoidance of doubt, references herein to "treatment" include references to curative, palliative and prophylactic treatment.

Syk kinase inhibitors, such as the compound of the invention, may advantageously be administered in combination with one or more other therapeutic agents, particularly in the treatment of respiratory diseases such as asthma. Examples of such further therapeutic agents include: (i) 5-lipoxygenase (5-LO) inhibitors or 5-lipoxygenase activating protein (FLAP) antagonists; (ii) leukotriene antagonists (LTRAs) including antagonists of $LTB_4$, $LTC_4$, $LTD_4$, and $LTE_4$; (iii) histamine receptor antagonists including $H_1$, $H_3$ and $H_4$ antagonists; (iv) $\alpha_1$- and $\alpha_2$-adrenoceptor agonist vasoconstrictor sympathomimetic agents for nasal decongestant use; (v) muscarinic $M_3$ receptor antagonists or anticholinergic agents; (vi) PDE inhibitors, e.g. $PDE_3$, $PDE_4$ and $PDE_5$ inhibitors; (vii) theophylline; (viii) sodium cromoglycate; (ix) COX inhibitors both non-selective and selective COX-1 or COX-2 inhibitors (NSAIDs); (x) oral and inhaled glucocorticosteroids, such as DAGR (dissociated agonists of the corticoid receptor); (xi) monoclonal antibodies active against endogenous inflammatory entities; (xii) anti-tumor necrosis factor (anti-TNF-$\alpha$) agents; (xiii) adhesion molecule inhibitors including VLA-4 antagonists; (xiv) kinin-$B_1$- and $B_2$-receptor antagonists; (xv) immunosuppressive agents; (xvi) inhibitors of matrix metalloproteases (MMPs); (xvii) tachykinin $NK_1$, $NK_2$ and $NK_3$ receptor antagonists; (xviii) elastase inhibitors; (xix) adenosine $A_{2a}$ receptor agonists; (xx) inhibitors of urokinase; (xxi) compounds that act on dopamine receptors, e.g. D2 agonists; (xxii) modulators of the $NF_{\kappa\beta}$ pathway, e.g. IKK inhibitors; (xxiii) modulators of cytokine signaling pathways such as a p38 MAP kinase or JAK kinase inhibitor; (xxiv) agents that can be classed as mucolytics or anti-tussive; (xxv) antibiotics; (xxvi) HDAC inhibitors; (xxvii) PI3 kinase inhibitors; (xxviii) $\beta$2 agonists; and (xxix) dual compounds active as $\beta_2$ agonists and muscarinic $M_3$ receptor antagonists. Preferred examples of such therapeutic agents include: (a) glucocorticosteroids, in particular inhaled glucocorticosteroids with reduced systemic side effects, flunisolide, triamcinolone acetonide, beclomethasone dipropionate, budesonide, fluticasone propionate, ciclesonide, and mometasone furoate; (b) muscarinic $M_3$ receptor antagonists or anticholinergic agents including ipratropium salts such as the bromide, tiotropium salts such as the bromide, oxitropium salts such as the bromide, perenzepine and telenzepine; and (c) $\beta_2$ agonists including salbutamol, terbutaline, bambuterol, fenoterol, salmeterol, formoterol, tulobuterol. Any of the agents specifically mentioned may optionally be used in the form of a pharmaceutically acceptable salt.

Where it is desirable to administer a combination of active compounds, two or more pharmaceutical compositions, at least one of which contains the compound of the invention, may conveniently be combined in the form of a kit suitable for co-administration.

Such a kit comprises two or more separate pharmaceutical compositions, at least one of which contains the compound of the invention, and means for separately retaining said compositions, such as a container, divided bottle, or divided foil packet. An example of such a kit is the familiar blister pack used for the packaging of tablets, capsules and the like.

Such a kit is particularly suitable for administering different dosage forms, for example, oral and parenteral dosage forms, for administering the separate compositions at different dosage intervals, or for titrating the separate compositions against one another. To assist compliance, the kit typically comprises directions for administration and may be provided with a so-called memory aid.

PREPARATIVE EXAMPLE

The following example illustrates the preparation of the xinafoate salt of N4-[(2,2-difluoro-4H-benzo[1,4]oxazin-3-one)-6-yl]-5-fluoro-N2-[3-(methylaminocarbonyl methyleneoxy)phenyl]-2,4-pyrimidinediamine.

A suspension of 2-{3-[4-(2,2-Difluoro-3-oxo-3,4-dihydro-2H-benzo[1,4]oxazin-6-ylamino)-5-fluoro-pyrimidin-2-ylamino]phenoxy}N-methyl-acetamide (1.18 kg, 2.49 mmol, 1 equiv) in methyl ethyl ketone (MEK) (23.6 L, 20 ml/g) was heated to 55° C., whereupon water (1.18 L, 1 ml/g) was added, resulting in a solution. The solution was passed through a filter for clarification then held at 55° C. for 1 hour. The subsequent addition of a pre-formed spec-free solution of 1-hydroxy-2-naphoic acid (515 g, 2.74 mol, 1.1 equiv) in MEK (4.72 L, 4 ml/g) resulted in precipitation of a white solid after ~10 mins. The reaction was cooled to ambient temp, stirred overnight (18 hours) and then cooled to 5° C. for 2 hours before filtration. The filtered solid was washed with MEK (2×2.36 L, 2×2 ml/g) and dried under reduced pressure at 50° C. for 16 hours. The product, 2-{3-[4-(2,2-difluoro-3-oxo-3,4-dihydro-2H-benzo[1,4]oxazin-6-ylamino)-5-fluoro-pyrimidin-2-ylamino]phenoxy}N-methyl-acetamide 1-hydroxy-2-naphoic acid salt, was isolated as a white solid (1.32 kg, 80%).

When analysed by conventional proton NMR (300 MHz, $d_6$-DMSO), the xinafoate salt gives the following spectrum: $\delta$ 2.65 (d, J=4.5 Hz, 3H), 4.34, (s, 2H), 6.46-6.52 (m, 1H), 7.10 (t, J 8.0 Hz, 1H), 7.23-7.28 (m, 2H), 7.36-7.41 (m, 2H), 7.45-7.48 (m, 1H), 7.55-7.62 (m, 2H), 7.64-7.71 (m, 1H), 7.73-7.77 (m, 1H), 7.86-7.95 (m, 2H), 8.14 (d, J 4.0 Hz, 1H), 8.26-8.32 (m, 1H), 9.14 (s, 1H), 9.56 (s, 1H), 11.90-11.96 (m, 1H).

Figure 1:
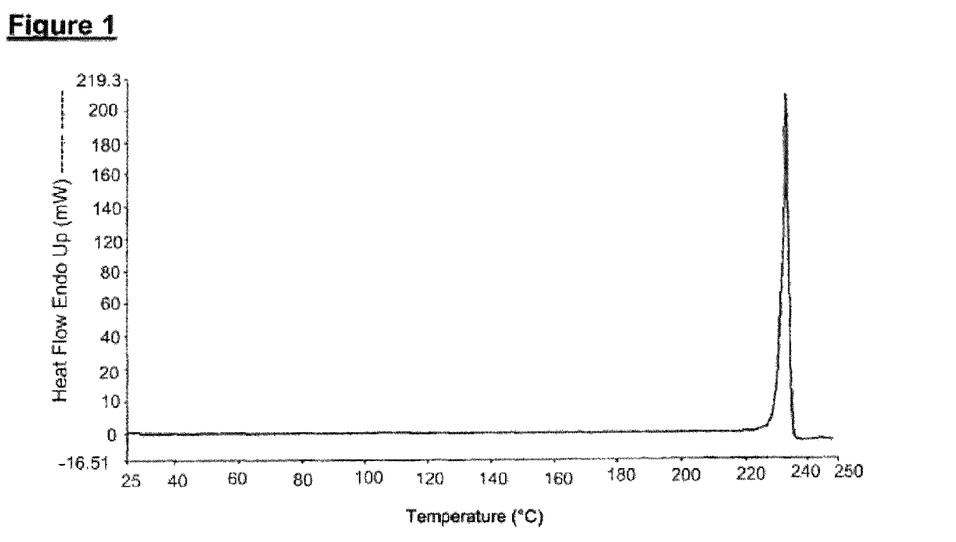
FIG. 1 is a differential scanning calorimetry trace of the xinafoate salt.

When analysed by differential scanning calorimetry (DSC) (8.588 mg of the sample was heated from 25 to 250° C. at 20° C. per minute using a Perkin Elmer Diamond DSC with autosampler and a 4 hole side wall vented aluminum pan and lid with nitrogen flow gas), the xinafoate salt shows a sharp endothermic melting peak at 233° C.±2° C. The DSC trace is shown in FIG. 1.

Figure 2:
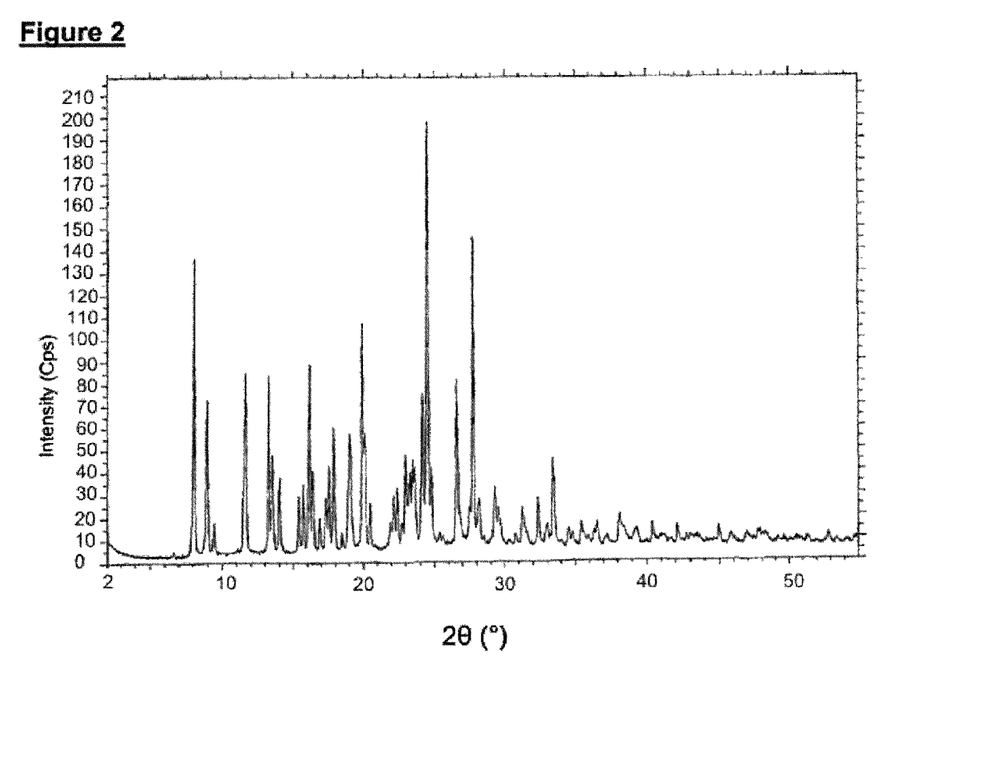
FIG. 2 is a powder X-ray diffraction pattern of the xinafoate salt.

When characterised by powder X-ray diffraction (PXRD), the xinafoate salt gives the pattern shown in FIG. 2. The characteristic peaks are given in Table 1 below. The main characteristic peaks are at 8.0, 8.9, 11.6, 24.5 and 27.7 degrees two theta (±0.1 degree).

TABLE 1

Characteristic PXRD peaks

| Angle 2-Theta (degrees) | Relative intensity (%) |
|---|---|
| 8.0 | 68.7 |
| 8.9 | 36.5 |
| 11.6 | 42.6 |
| 13.2 | 42.5 |
| 13.5 | 23.8 |
| 14.0 | 18.7 |
| 15.3 | 15.0 |
| 15.6 | 17.4 |
| 16.1 | 44.5 |
| 16.4 | 20.1 |
| 17.3 | 14.5 |
| 17.5 | 21.4 |
| 17.8 | 30.3 |
| 19.0 | 28.9 |
| 19.8 | 54.0 |
| 20.0 | 28.8 |
| 20.4 | 13.0 |
| 22.1 | 15.0 |
| 22.4 | 16.5 |
| 23.0 | 24.1 |
| 23.2 | 19.9 |
| 23.5 | 22.8 |
| 23.6 | 20.9 |
| 24.1 | 38.1 |
| 24.5 | 100.0 |
| 24.7 | 20.6 |
| 26.6 | 41.1 |
| 27.5 | 12.3 |
| 27.7 | 73.7 |
| 28.1 | 14.1 |
| 29.3 | 16.6 |
| 29.5 | 11.4 |
| 31.2 | 11.8 |
| 32.4 | 14.4 |
| 33.4 | 22.5 |

The powder X-ray diffraction pattern was determined using a Bruker-AXS Ltd D4 powder X-ray diffractometer fitted with an automatic sample changer, a theta-theta goniometer, automatic beam divergence slit, and a PSD Vantec-1 detector. The sample was prepared for analysis by mounting on a low background silicon wafer specimen mount. The specimen was rotated whilst being irradiated with copper K-alpha 1 X-rays (wavelength=1.5406 Ångstroms) with the X-ray tube operated at 40 kV/30 mA. The analyses were performed with the goniometer running in continuous mode set for a 0.2 second count per 0.018° step over a two theta range of 2° to 55°. Peaks were selected manually using Bruker-AXS Ltd evaluation software. The data were collected at 21° C.

As will be appreciated by the skilled person, the relative intensities of the various peaks within Table 1 given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Table 1. The skilled person will also appreciate that measurements using a different wavelength will result in different shifts according to the Bragg equation—$n\lambda=2d \sin \theta$. Such alternative PXRD patterns generated by use of alternative wavelengths are nevertheless representations of the same material.

Figure 3:
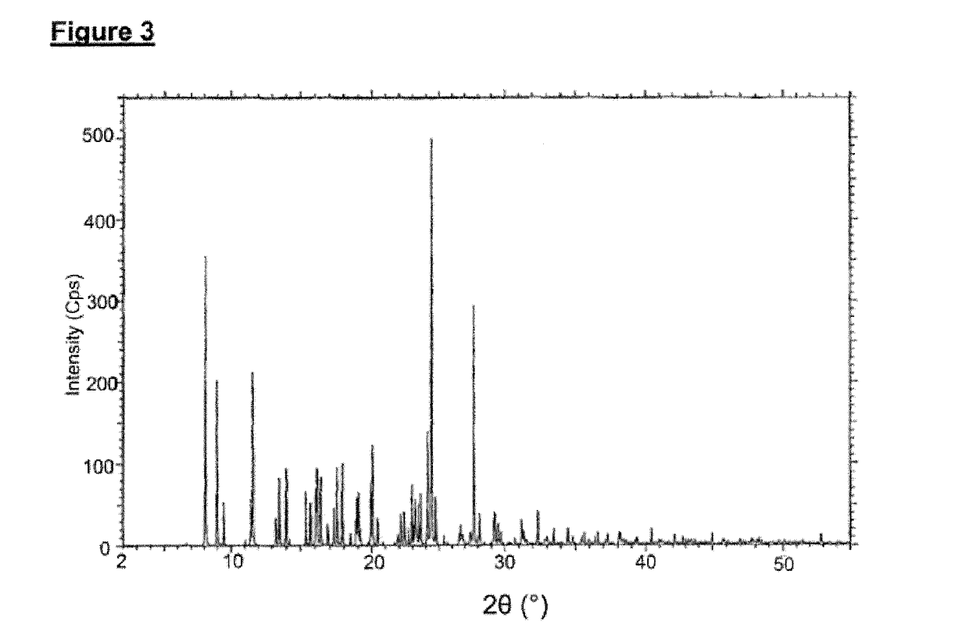
FIG. 3 is a simulated crystal X-ray analysis of the xinafoate salt.

The main PXRD peaks which have been simulated from a single crystal X-ray analysis are listed in Table 2 below and the corresponding simulated pattern is shown in FIG. 3.

TABLE 2

Characteristic simulated PXRD peaks

| Angle 2-Theta (degrees) | Relative intensity (%) |
|---|---|
| 8.0 | 72.5 |
| 8.9 | 41.3 |
| 9.4 | 10.5 |
| 11.4 | 11.5 |
| 11.6 | 43.0 |
| 13.5 | 16.6 |
| 14.0 | 19.2 |
| 15.3 | 13.3 |
| 15.7 | 10.2 |
| 16.0 | 14.3 |
| 16.1 | 17.6 |
| 16.4 | 17.1 |
| 17.5 | 19.4 |
| 17.9 | 20.3 |
| 18.9 | 11.7 |
| 19.0 | 13.2 |
| 19.9 | 15.8 |
| 20.1 | 25.1 |
| 23.0 | 15.2 |
| 23.2 | 11.5 |
| 23.5 | 10.2 |
| 23.6 | 12.1 |
| 24.1 | 28.5 |
| 24.4 | 14.1 |
| 24.5 | 100.0 |
| 24.7 | 11.9 |
| 27.7 | 58.5 |

Figure 4:
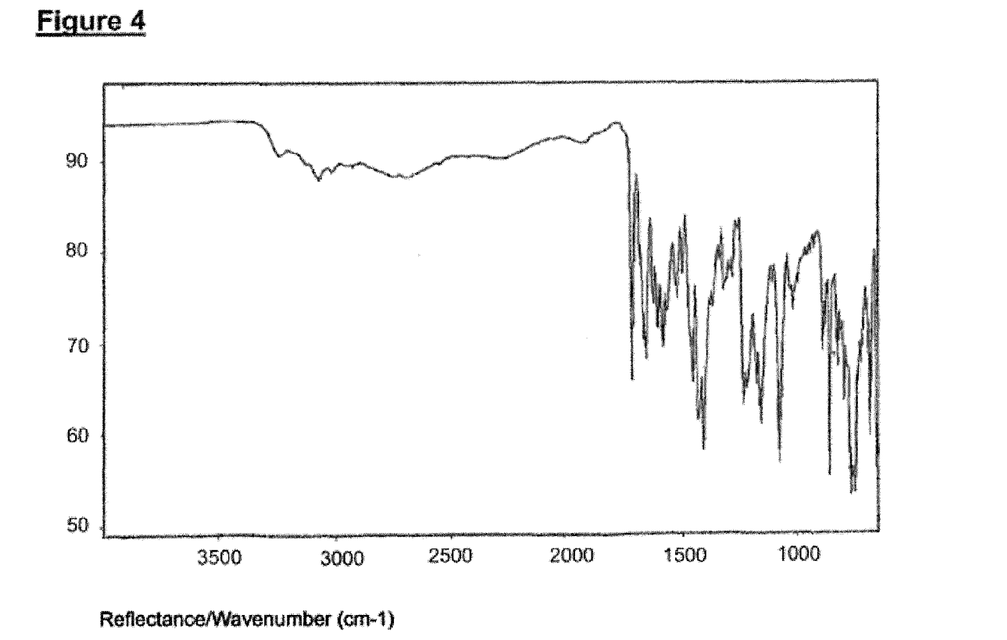
FIG. 4 is a Fourier Transform IR spectrum of the xinafoate salt.
Figure 5:
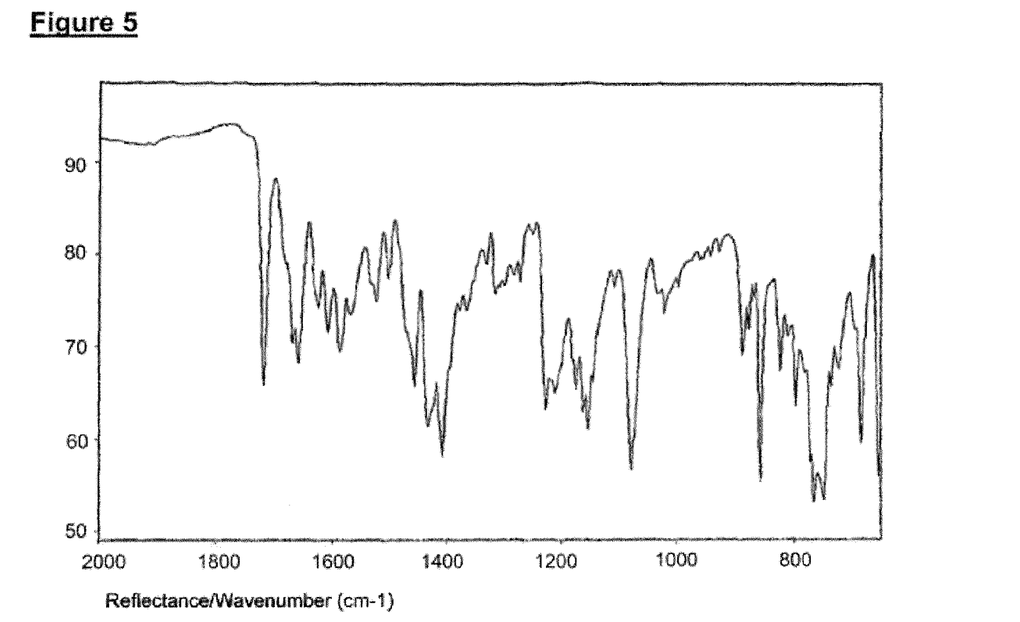
FIG. 5 is a fingerprint region of the FIRT spectrum of FIG. 4.

When characterised by Fourier Transform Infra-red (FT-IR) spectroscopy, the xinafoate salt gives the pattern shown in FIG. 4. The fingerprint region is shown in expanded form in FIG. 5. The characteristic peaks are given in Table 3 below (w=weak, s=strong, m=medium). The main characteristic peaks are 1228 (m), 1152 (m), 1078 (s) and 858 (s).

TABLE 3

Characteristic FT-IR peaks
Wavenumber (cm$^{-1}$)

| |
|---|
| 3230* (w) |
| 3069 (w) |
| 3015 (w) |
| 1717 (s) |
| 1669 (m) |
| 1659 (m) |
| 1625 (m) |
| 1608 (m) |
| 1587 (m) |
| 1569 (m) |
| 1523 (m) |

TABLE 3-continued

Characteristic FT-IR peaks
Wavenumber (cm$^{-1}$)

1501 (w)
1455 (m)
1431 (s)
1407 (s)
1364 (w)
1331 (w)
1316 (w)
1283 (w)
1272 (w)
1228 (m)
1212 (m)
1174 (m)
1161 (m)
1152 (m)
1107 (w)
1078 (s)
1020 (w)
928 (w)
888 (m)
877 (w)
858 (s)
823 (m)
810 (w)
796 (m)
764 (s)
747 (s)
734 (w)
721 (w)
683 (m)
653 (m)

The FT-IR spectrum was acquired using a ThermoNicolet Nexus FTIR spectrometer equipped with a 'DurasamplIR' single reflection ATR accessory (diamond surface on zinc selenide substrate) and d-TGS KBr detector. The spectrum was collected at 2 cm$^{-1}$ resolution and a co-addition of 256 scans for all compounds. Happ-Genzel apodization was used. Because the FT-IR spectrum was recorded using single reflection ATR, no sample preparation was required. Using ATR FT-IR will cause the relative intensities of infrared bands to differ from those seen in a transmission FT-IR spectrum using KBr disc or nujol mull sample preparations. Due to the nature of ATR FT-IR, the bands at lower wavenumber are more intense than those at higher wavenumber. Experimental error, unless otherwise noted, was ±2 cm$^{-1}$. Peaks were picked using ThermoNicolet Omnic 6.0a software.

Figure 6:
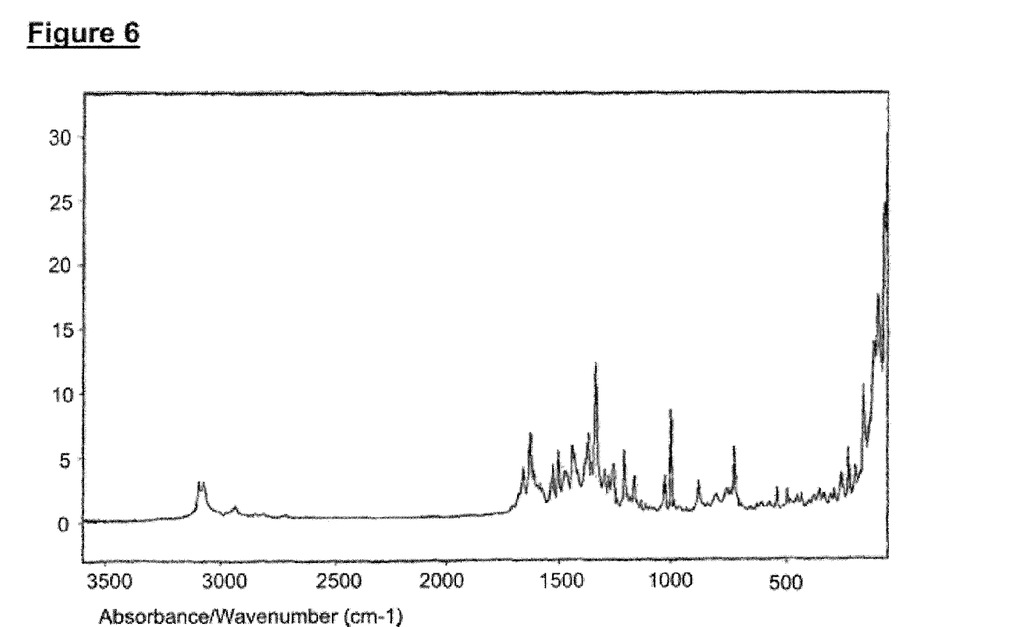
FIG. 6 is a Fourier transform Raman spectrum of the xinafoate salt.
Figure 7:
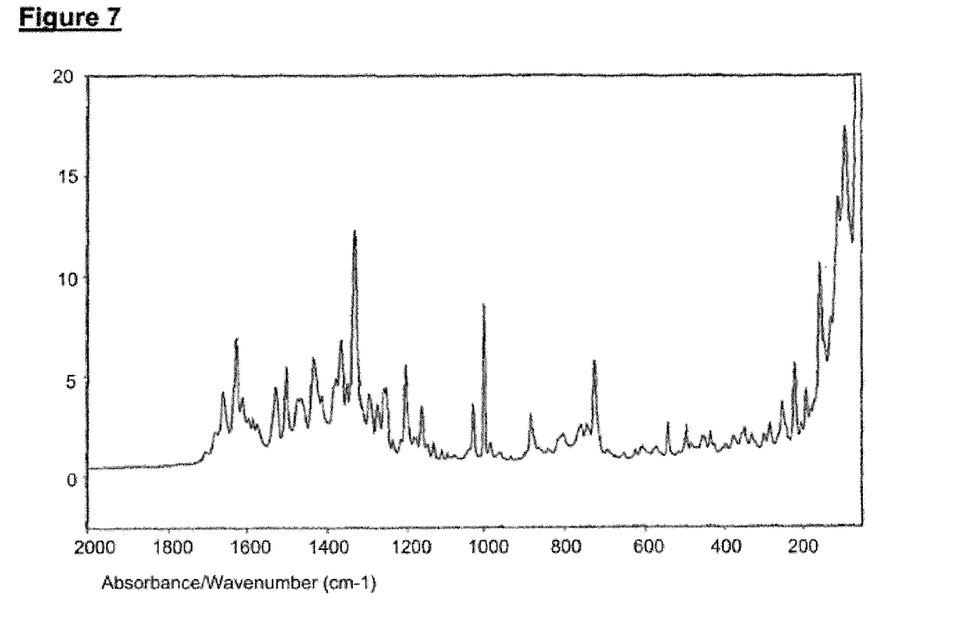
FIG. 7 is a fingerprint region of the Fourier Transform Raman spectrum of FIG. 6.

When characterised by Fourier Transform Raman spectroscopy, the xinafoate salt gives the pattern shown in FIG. 6. The fingerprint region is shown in greater detail in FIG. 7. The characteristic peaks are given in Table 4 below (w=weak, s=strong, m=medium). The main characteristic peaks are 1626 (m), 1205 (m), 998 (s), 156 (s) and 91 (s).

TABLE 4

Characteristic FT-Raman peaks

| Wavenumber (cm$^{-1}$) | Wavenumber (cm$^{-1}$) |
|---|---|
| 3092 (w) | 1473 (w) |
| 3071 (w) | 1465 (w) |
| 1679 (w) | 1434 (m) |
| 1659 (m) | 1414 (w) |
| 1626 (m) | 1379 (m) |
| 1161 (w) | 1365 (m) |
| 1596 (w) | 1353 (m) |
| 1584 (w) | 1333 (s) |
| 1574 (w) | 1296 (m) |
| 1525 (m) | 1276 (w) |
| 1502 (m) | 1260 (m) |

TABLE 4-continued

Characteristic FT-Raman peaks

| Wavenumber (cm$^{-1}$) | Wavenumber (cm$^{-1}$) |
|---|---|
| 1253 (m) | 332 (w) |
| 1205 (m) | 302 (w) |
| 1162 (w) | 286 (w) |
| 1026 (w) | 253 (w) |
| 998 (s) | 221 (m) |
| 879 (w) | 192 (w) |
| 726 (m) | 156 (s) |
| 542 (w) | 130 (m) |
| 495 (w) | 110 (s) |
| 434 (w) | 91 (s) |
| 352 (w) | 62 (s) |

The Raman spectrum was collected using a Bruker Vertex70 with RamII module FT-Raman spectrometer equipped with a 1064 nm NdYAG laser and LN-Germanium detector. The spectrum was recorded using 2 cm−1 resolution and Blackman-Harris 4-term apodization. Laser power was 300 mW and 2048 co-added scans were collected. Each sample was placed in a glass vial and exposed to the laser radiation. The data is presented as intensity as a function of Raman shift and is corrected for instrument response and frequency dependent scattering using a white light spectrum from a reference lamp. The Bruker Raman Correct function was used to do the correction. (Bruker software—OPUS 6.0). Experimental error, unless otherwise noted, was ±2 cm−1. Peaks were picked using ThermoNicolet Omnic 6.0a software.

Figure 8:
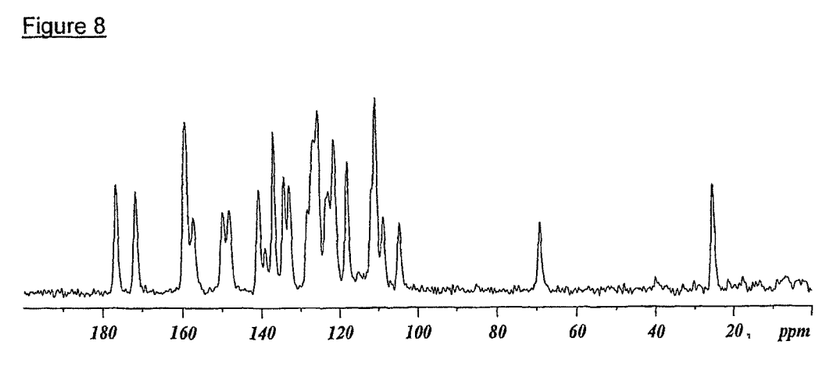
FIG. 8 is a proton decoupled $C^{13}$ solid state NMR of the xinafoate salt.

When characterised by proton decoupled $^{13}$C solid state NMR, the xinafoate salt gives the spectrum shown in FIG. 8. The characteristic shifts are given in Table 5 below. The main characteristic shifts are 176.8, 159.4, 137.1, 118.2, 104.9 and 25.4 ppm. Intensities can vary depending on the actual setup of the experimental parameters and the thermal history of the sample and are not therefore necessarily quantitative.

TABLE 5

Characteristic $^{13}$C solid state NMR shifts

| Chemical shift (ppm) | Intensity |
|---|---|
| 176.8 | 6.48 |
| 171.8 | 6.04 |
| 159.4 | 10.46 |
| 157.5 | 4.33 |
| 150.0 | 4.66 |
| 148.3 | 4.83 |
| 140.9 | 6.12 |
| 139.2 | 2.37 |
| 137.1 | 9.88 |
| 134.4 | 6.97 |
| 133.1 | 6.41 |
| 128.4 | 4.88 |
| 126.9 | 9.39 |
| 125.8 | 11.22 |
| 123.0 | 6.03 |
| 121.6 | 9.38 |
| 118.2 | 7.96 |
| 110.9 | 12 |
| 109.0 | 4.37 |
| 104.9 | 3.99 |
| 69.3 | 4.01 |
| 25.4 | 6.37 |

Approximately 80 mg of sample were tightly packed into a 4 mm ZrO$_2$ spinner. The spectrum was collected at ambient conditions on a Bruker-Biospin 4 mm BL HFX CPMAS probe positioned into a wide-bore Bruker-Biospin Avance DSX 500 MHz NMR spectrometer. The sample was positioned at the magic angle and spun at 15.0 kHz. The fast spinning speed minimized the intensities of the spinning side bands. The number of scans was adjusted to obtain adequate S/N. The $^{13}$C solid state spectrum was collected using a proton decoupled cross-polarization magic angle spinning experiment (CPMAS). A proton decoupling field of approximately 85 kHz was applied. 656 scans were collected with the recycle delay adjusted to 80 seconds. The spectrum was referenced using an external standard of crystalline adamantane, setting its upfield resonance to 29.5 ppm.

Figure 9:
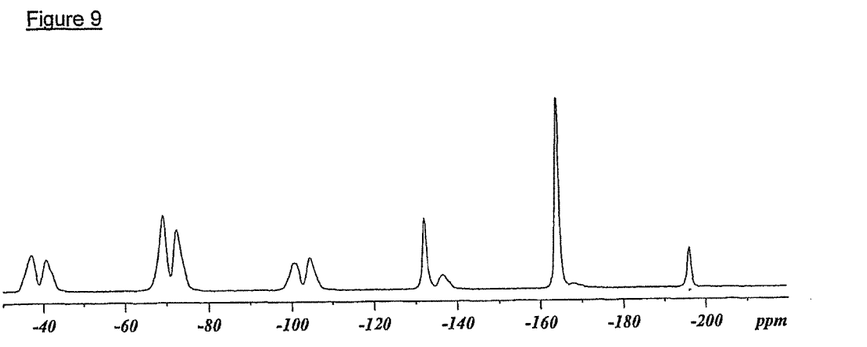
FIG. 9 is a fluorine solid state NMR of the xinafoate salt.

When characterised by fluorine solid state NMR, the xinafoate salt gives the spectrum shown in FIG. 9. The characteristic shifts are −69.2, −72.4 and −164.0 ppm. Intensities can vary depending on the actual setup of the experimental parameters and the thermal history of the sample and are not therefore necessarily quantitative.

The same apparatus was used to acquire the fluorine NMR spectrum as that used to acquire the $^{13}$C spectrum. The $^{19}$F solid state spectrum was collected using a proton decoupled magic angle spinning (MAS) experiment. The proton decoupling field of approximately 85 kHz was applied and 8 scans were collected. The recycle delay was set to 750 s to ensure acquisition of quantitative spectra. Proton longitudinal relaxation times ($^1$H T$_1$) were calculated based on a fluorine detected proton inversion recovery relaxation experiment. Fluorine longitudinal relaxation times ($^{19}$F T$_1$) were calculated based on a fluorine detected fluorine inversion recovery relaxation experiment. The spectrum was referenced using an external sample of trifluoroacetic acid (50% by volume in H$_2$O), setting its resonance to −76.54 ppm.

Stability Data

In contrast to the free base, the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine is essentially non-hygroscopic. Hygroscopicity was assessed using dynamic vapour sorption equipment (Surface Measurement Systems Ltd, model DVS-1). The analysis was conducted at 30° C. with a nitrogen gas flow of 200 cc/min. Water sorption and desorption were determined in the range 0 to 90% relative humidity (RH) using 15% RH intervals. Exposure was for a minimum of 2 hours at each humidity or until the rate of weight change was less than 0.0003%/minute (averaged over 10 minutes). Sample weight was 12.6 mg. The sample was weighed using a CAHN D-200, seven place digital recording balance, which is an integral part of the equipment. The compound showed only 0.6% water sorption at 90% RH. Furthermore, following micronisation using jet milling, there was no change in solid form, a negligible decrease in the degree of crystallinity and no significant change in hygroscopicity (0.9% water sorption at 90% relative humidity).

Furthermore, the xinafoate salt does not show any hydration or salvation. Solvation/Hydration was assessed by thermogravimetric analysis (TGA) using a TA Instruments Hi-Res TGA 2950 instrument measuring the weight loss of a 8.8 mg sample in an open platinum pan. The sample was heated at 20° C./min from ambient to 300° C. utilizing a nitrogen furnace purge gas. Whereas a single form of the xinafoate salt has hitherto been identified, the free base hydrates to form a hemihydrate and formed a different solvated form in each of nine solvents tested.

In order to test for solid state stability and excipient compatibility, a sample of the xinafoate salt was micronised by jet milling (particle size: D10=0.24 μm, D50=1.15 μm, D90=4.29 μm) and the resulting powder was blended at a 1:100 weight ratio with lactose monohydrate (Respitose grade SV008). Samples were stored for 12 weeks at 25° C./60% relative humidity and 40° C./75% relative humidity and assayed for remaining drug content and impurities at 4, 8 and 12 weeks. The results are shown in Table 6. A control sample was stored at 5° C./0% humidity.

TABLE 6

Stability data

| | % main band remaining versus control | | |
|---|---|---|---|
| Sample | 4 weeks | 8 weeks | 12 weeks |
| 25° C./60% RH | 100.2 | 99.9 | 100.1 |
| 40° C./75% RH | 100.4 | 100.0 | 100.0 |

The results show that lactose blends of the xinafoate salt have good stability. During the experiment, no change in physical form was detected and no significant degradation was observed.

The invention claimed is:

1. A method for treating a disease for which a Syk inhibitor is indicated in a mammal comprising administering to the mammal in need thereof a therapeutically effective amount of the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine.

2. The xinafoate salt of claim 1 having shifts at about −69.2, −72.4 and −164.0 ppm when characterized by fluorine solid state NMR referenced to an external sample of trifluoroacetic acid (50% by volume in H$_2$O) assigned a resonance at −76.54 ppm.

* * * * *

UNITED STATES PATENT AND TRADEMARK OFFICE
CERTIFICATE OF CORRECTION

PATENT NO.        : 8,486,935 B2
APPLICATION NO.   : 13/467850
DATED             : July 16, 2013
INVENTOR(S)       : Stefan Colin John Taylor Page 1 of 1

It is certified that error appears in the above-identified patent and that said Letters Patent is hereby corrected as shown below:

In the claims:

Column 22, Claim 1, lines 39-44

"1.    A method for treating a disease for which a Syk inhibitor is indicated in a mammal comprising administering to the mammal in need thereof a therapeutically effective amount of the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine."

should read:

--1.    A method for treating asthma in a mammal comprising administering to the mammal in need thereof a therapeutically effective amount of the xinafoate salt of N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine.--

Column 22, Claim 2, lines 45-49

"2.    The xinafoate salt of claim 1 having shifts at about -69.2, -72.4 and -164.0 ppm when characterized by fluorine solid state NMR referenced to an external sample of trifluoroacetic acid (50% by volume in $H_2O$) assigned a resonance at -76.54 ppm."

should read:

--2.    The method of claim 1, wherein the xinafoate salt has shifts at about -69.2, -72.4 and -164.0 ppm when characterized by fluorine solid state NMR referenced to an external sample of trifluoroacetic acid (50% by volume in $H_2O$) assigned a resonance at -76.54 ppm.--

Signed and Sealed this
Twenty-fourth Day of September, 2013

Teresa Stanek Rea
*Deputy Director of the United States Patent and Trademark Office*